United States Patent [19]
Whittaker

[11] Patent Number: 4,972,946
[45] Date of Patent: Nov. 27, 1990

[54] DISPOSABLE DENTAL HYGIENE KIT

[76] Inventor: Dale Whittaker, 1329 Quail Run Cir., Bentonville, Ark. 72712

[21] Appl. No.: 461,846

[22] Filed: Jan. 8, 1990

[51] Int. Cl.$^5$ ........................ A45D 40/24; B65D 85/00
[52] U.S. Cl. ..................................... 206/210; 132/324; 206/388; 206/368; 206/581
[58] Field of Search ............... 132/308, 309, 321, 323, 132/324; 206/63.3, 63.5, 361, 368, 388, 438, 581, 823, 210

[56] References Cited

U.S. PATENT DOCUMENTS

| | | | |
|---|---|---|---|
| 2,176,308 | 10/1939 | Larkin | 206/63.5 |
| 3,357,549 | 12/1967 | Staiti | 206/63.3 |
| 4,211,330 | 7/1980 | Strock | 206/63.5 |
| 4,530,129 | 7/1985 | Labick et al. | 206/63.5 |
| 4,579,221 | 4/1986 | Corella | 206/63.5 |
| 4,588,089 | 5/1986 | Yanz, Jr. et al. | 206/63.5 |
| 4,836,227 | 6/1989 | Charatan | 132/324 |
| 4,852,728 | 8/1989 | Court | 206/63.5 |

FOREIGN PATENT DOCUMENTS 0633709 12/1982 Switzerland ....................... 206/63.5

*Primary Examiner*—Jimmy G. Foster
*Attorney, Agent, or Firm*—Robert R. Keegan

[57] ABSTRACT

There is disclosed a dental hygiene kit including a sealed flat rectangular package formed of a pair of foil lined synthetic plastic sheets sealed together around all the edges thereof and having an end portion which is tearable to open the package. Within the package is a synthetic felt pad about 3.5 by 7.0 by 0.2 cm. folded once to form a square; within the folded synthetic felt pad is approximately 30 cm. of unwaxed dental floss wound on a plastic or paper spindle about 3 cm. by 1 cm. The pad is impregnated with about two cc of liquid consisting of water, about 15% alcohol, and a dentafrice consisting of one or more of the substances thymol, eucalyptol, menthol or benzoic acid. As an alternative to the spindle for the dental floss, the floss may be contained in a transparent plastic bag about 2.5 by 3.0 cm. or may simply be wound in a flat spiral coil. The kit is used by tearing open one end, removing and using the dental floss in a customary manner, and wiping the teeth with the felt pad in lieu of a toothbrush.

16 Claims, 1 Drawing Sheet

DISPOSABLE DENTAL HYGIENE KIT

The present invention relates to packs or kits containing dental hygiene materials such as dental floss or tooth cleaning pads with dentifrice solution impregnating the floss or pad. More particularly the present invention provides a small hermetically sealed pack which is easily opened to extract a length of dental floss suitable for one time use together with a folded synthetic felt pad for wiping the teeth, both of which are impregnated with a water, alcohol, dentifrice solution. An important feature of the disposable dental hygiene kit according to the invention is its simplicity and hence the ease with which it may be manufactured and the low cost at which it may be provided to the consumer.

While dental hygiene kits have been known before, they have not combined the small convenient size and economy which can be achieved with the apparatus of the present invention. By use of the disposable dental hygiene kit according to the present invention the user may attend to cleaning the teeth after meals when away from home without carrying a bulky toothbrush or dental floss container and at the same time incurring very little expense for purchase of the disposable kits.

Among the previous endeavors to provide a disposable dental kit is the apparatus shown in U.S. Pat. No. 4,105,120 to Bradberry (U.S. Cl. 206/581). The pack disclosed by Bradberry is formed of biodegradable paper sheets 12 and 14. Since the package does not appear to be hermetically sealed, the package provides a solid dentifrice such as tooth powder which is activated by the saliva of the user (column 1 lines 62-65); a very short length of dental floss 34 is secured in a dental floss holder. It will also be noted that the dental floss holder and scrubber structure of Bradberry is a complex structure which would be relatively costly to manufacture compared with the simple structure of the present invention.

A dental floss container in which the dental floss is impregnated with a liquid or semi-liquid fluoride solution is shown in the patent to Elbreder, U.S. Pat. No. 4,019,522 (U.S. Cl. 132/90) The apparatus of Elbreder is clearly not a disposable, one use package and would not provide the advantages of the present invention. Hermetically sealed packs for filaments are shown in U.S. Pat. No 2,824,642 to Stoltz (U.S. Cl. 206/63.3) but the Stoltz pack is designed for surgical sutures and the objective of Stoltz is to provide an absolutely sterile and contamination proof removal system for surgical sutures. The package of Stoltz would not be adaptable for the purposes of the present invention. Individual dental floss packages are shown in U.S. Pat. No. 4,693,365 to Corella (U.S. Cl. 206/63.3) The Corella package does not include a tooth wiping pad as does the package of the present invention and it would not be adaptable to the inclusion of such a pad.

It will be seen therefore that the present invention provides an improved disposable dental hygiene apparatus wherein the requirements for a tooth brushing or wiping means and means for flossing are met with notable simplicity and economy of manufacture. Impregnation of the dental floss and the pad with a dentifrice and antibacterial solution further enhances the effectiveness of the dental hygiene kit of the present invention.

In addition to providing the features and advantages described above it is an object of the present invention to provide a simple, inexpensive dental hygiene kit including a pad of about $4 \times 8$ cm. impregnated with a solution suitable for oral use to wipe the tooth surfaces.

It is another object of the present invention to provide a hermetically sealed, easily opened, disposable package containing a suitable one time use length of dental floss impregnated with an antibacterial solution of alcohol or the like.

It is still another object of the present invention to provide a dental hygiene kit including a tearable hermetically sealed plastic package no more than about 1 cm. thick or about 6 cm. square having a folded pad of synthetic felt material therein with a spindle within the folds of the pad having about 30 cm. of dental floss wound thereon.

Other objects and advantages will be apparent from consideration of the following description in conjunction with the appended drawings in which.

Figures 1, 2:
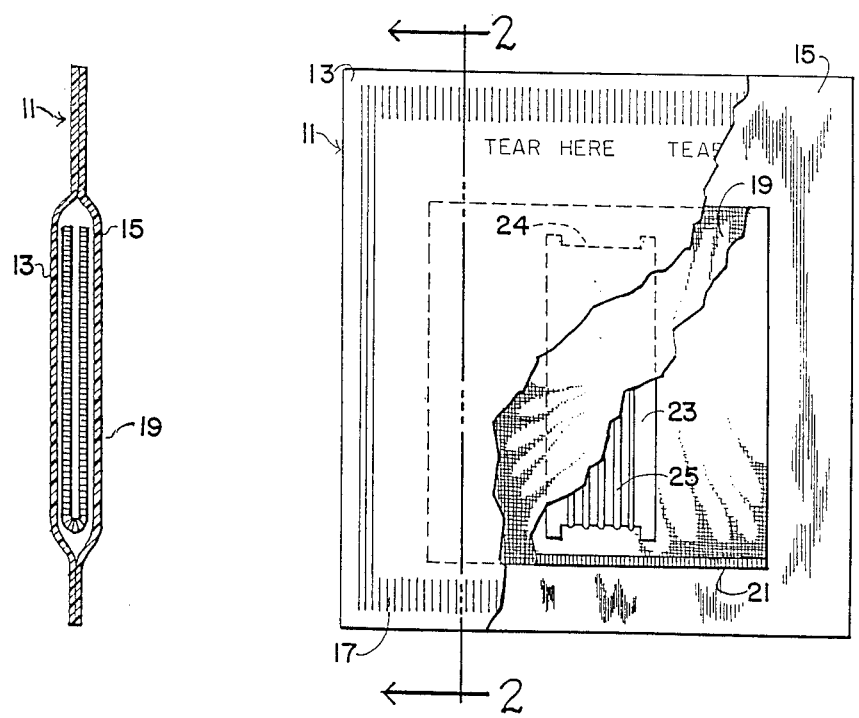
FIG. 1 is a plan view partially broken away showing a preferred form of disposable dental hygiene kit according to the invention.
FIG. 2 is a sectional view of the apparatus of FIG. 1 taken along the line 2—2 in FIG. 1.

Referring now to the drawings and particularly FIGS. 1 and 2, a disposable dental hygiene kit 11 is shown with an outer package formed of two rectangular plastic sheets 13 and 15 which are heat and/or pressure sealed in conventional manner on a seal line 17 extending around all sides of the sheets 13 and 15. Sheets 13 and 15 may be approximately 0.1 mm. thick and may be formed of any vinyl plastic or other plastic commonly used for such packaging applications and capable of being readily torn. If desired the sheets 13 and 15 may be provided with a notch (not shown) to facilitate starting a tear across the top of the package of FIG. 1 through the portion bearing the legend TEAR HERE.

When sealed as shown in FIG. 1 and FIG. 2 the package will be substantially hermetically sealed effectively preventing the escape of any liquids or vapors from the package. Within the sealed package is a synthetic felt pad 19 of non-woven material which may typically be of oblong rectangular shape about 3.5 cm. by 7 cm. with a thickness of approximately 0.2 cm. The felt pad 19 is folded across its width as shown at 21 so that the folded pad is approximately square in shape. Within the folds of pad 19 is a spindle 23 having wound thereon a strand of conventional (preferably unwaxed) dental floss 25 with a length of about 30-50 cm. Preferably spindle 23 has an indentation 24 in each end to provide a better carrier for the dental floss 25. Dental floss 25 may be shorter but preferably no shorter than 15 cm.

Figures 3, 4, 5:
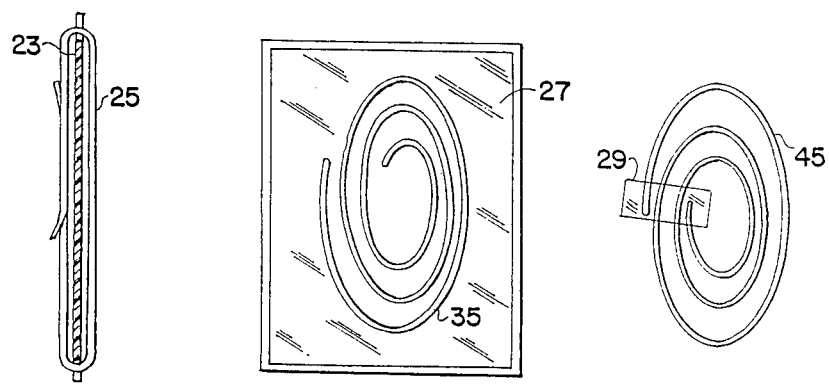
FIG. 3 is a sectional view of the spindle of dental floss of FIG. 1.
FIG. 4 is a plan view of an alternative dental floss holder for substitution in the apparatus of FIG. 1.
FIG. 5 is a further alternative form of dental floss holder for inclusion in the package of FIG. 1.

A sectional view of the spindle 23 as shown in FIG. 3 illustrating the manner in which the dental floss 25 is wrapped on the spindle 23, which may be of rigid or semi-rigid plastic sheet material of a thickness from 0.2 mm. to 1 mm. for example. Alternatively the spindle may be formed of plastic-coated or uncoated paperboard.

FIG. 4 shows an alternative method of retaining the dental floss 35 for easy positioning within the folds of the pad 19. The strand of dental floss 35 is coiled and enclosed in a plastic envelope 27 sealed on at least three sides and preferably formed of transparent material. The strand of dental floss 35 may be shorter or longer than illustrated in FIG. 4, it also being understood that all illustrations show the dental hygiene kit and its components slightly larger than actual size.

FIG. 5 shows a further alternative means for securing a dental floss strand 45 in a spiral configuration for replacement in the package of FIG. 1. In FIG. 5 the dental floss 45 is retained by an adhesive strip 29 which may be either transparent or opaque. It will be understood that the alternative embodiments represented by FIG. 4 or FIG. 5 would replace spindle 23 and dental floss 25 in FIG. 1, all other aspects of the illustration in FIG. 1 being the same.

While it is desirable that the kit according to the present invention be compact to facilitate carrying in the pocket or purse, the size is not specially critical and the width of an unfolded pad 19 may range from 2 cm. to about 5 cm. and its length from about 5 cm. to about 10 cm.; preferably the overall size of the package should not exceed about 8 cm. in length and somewhat less in width. Although the rectangular shape shown is preferable for the pad 19 and the overall package 11, a different shape could be selected if desired; for example, the corners could be rounded rather than 90° angles as shown.

Also the method of sealing the edges of the pack is subject to variation. Clearly, the two sheets 13 and 15 could be replaced by a single sheet folded over so that only three sides would need to be sealed. The sealing may be accomplished with adhesive as well, or in place of heat or pressure. An advantage of the particular arrangement shown is the availability of manufacturing equipment to rapidly produce packages sealed with solid and/or liquid contents. While the felt pad 19 in the preferred embodiment is a synthetic non-woven felt pad of smooth texture produced by fine fibers, a woven or non-woven pad of coarser texture could be employed to provide more scrubbing action on the teeth.

The pad 19 having a single fold across its width is believed to be a most satisfactory configuration; however, the pad could be folded more than once to be three or four thickness thick if that was found to be desirable.

The liquid with which the pad 19 and/or floss 25 is impregnated is subject to wide variation but will normally have for its primary constituents water and about 10% to 20% alcohol (of non-toxic medicinal type such as ethanol). The other ingredients may be selected from among thymol, eucalyptol, menthol, and benzoic acid. This dentifrice liquid may in fact be of any form and may include antibacterial compositions tending to prevent the growth of deleterious bacteria contributing to the formation of tartar, halitosis, or the like.

Instructions for use of the pack may be included or may be imprinted on the pack itself, but the use of the hygiene kit is simple and requires no detailed explanations. For example, the dental floss is used in a customary manner after being unwound and is of sufficient length to be held between the thumb and finger of the users right and left hands in conventional fashion. The pad 19 is backed up by a finger or thumb and used to wipe all accessible surfaces of the teeth to remove food particles or liquid food residues. As customary, the impregnating liquid may have ingredients added as necessary to provide a pleasant taste and odor.

In addition to the modifications and variations to the invention described above, other modifications and variations will be apparent to those skilled in the art and accordingly the invention is not to be considered limited to the particular embodiments shown, described or suggested but rather the scope of the invention is to be determined by reference to the appended claims.

What is claimed is:

1. An individual dental hygiene pack comprising
   a sheet of non-woven liquid absorbent fabric with a width of from about 2 cm. to about 5 cm. and a length from about 5 cm. to about 10 cm.,
   a length of dental floss of at least about 15 cm., said sheet being folded to enclose said dental floss
   said sheet being impregnated with about 0.5 to 5.0 cc. of non-toxic liquid predominantly composed of alcohol and water, and
   a substantially air tight package of flexible material enclosing said sheet and floss to form a generally flat, approximately square package, said package having at least one portion of which is tearable to permit opening thereof to remove said sheet and dental floss.

2. Apparatus as recited in claim 1 wherein said liquid further comprises a dentifrice selected from the group consisting of thymol, eucalyptol, menthol, and benzoic acid.

3. Apparatus as recited in claim 1 wherein said liquid further includes a dentifrice ingredient.

4. Apparatus as recited in claim 1 wherein said sheet of nonwoven liquid absorbent fabric is a synthetic fiber pad with a width of about 3 cm. to about 4 cm., a length of about 6 cm. to about 8 cm., and a thickness of about 0.5 cm. to about 1.5 cm.

5. Apparatus as recited in claim 1 wherein said package of flexible material is formed of tearable foil-lined synthetic plastic lower and upper sheets sealed together around all edges thereof.

6. A dental hygiene kit comprising;
   an envelope,
   a folded sheet of tooth cleaning material disposed in said envelope,
   a strand of dental floss disposed in said folded sheet of tooth cleaning material and,
   a dentifrice material impregnating said tooth cleaning sheet of material.

7. Apparatus as recited in claim 6 further including a flat sheet in the form of a spindle and wherein said floss is wound on said spindle.

8. Apparatus as recited in claim 6 further including a bag formed of flexible transparent plastic material disposed in said folded sheet of tooth cleaning material and at least partially enclosing said strand of dental floss.

9. Apparatus as claimed in claim 6 wherein said dentifrice material is a non-toxic liquid predominantly composed of alcohol and water.

10. Apparatus as recited in claim 6 wherein said envelope is formed of two substantially rectangular sheets of flexible, tearable plastic material sealed together around all four edges thereof.

11. An individual dental hygiene pack comprising
    a sheet of flexible fabric with a width of no less than about 2 cm. to about 5 cm. and a length no less than 5 cm. to about 10 cm.,
    a length of dental floss of no less than about 15 cm., said sheet being folded to enclose said dental floss,
    said sheet being impregnated with no less than about one cc. liquid comprising alcohol and water, and
    a substantially air tight package of flexible material enclosing d sheet and floss to form a generally flat package, said package having means to permit opening thereof in order to remove said sheet and dental floss.

12. Apparatus as recited in claim 11 wherein said liquid further comprises a dentifrice ingredient selected from the group consisting of thymol, eucalyptol, menthol, and benzoic acid.

13. Apparatus as recited in claim 11 wherein said liquid further includes a dentifrice ingredient.

14. Apparatus as recited in claim 11 wherein said sheet of flexible fabric is a synthetic fiber pad with a width of about 3 cm. to about 4 cm., a length of about 6 cm. to about 8 cm., and a thickness of about 0.5 cm. to about 1.5 cm.

15. Apparatus as recited in claim 11 wherein said package of flexible material is formed of tearable foil-lined synthetic plastic lower and upper sheets sealed together around all eges thereof.

16. Apparatus as recited in claim 11 further including a bag formed of flexible transparent plastic material disposed in said folded sheet of tooth cleaning material and at least partially enclosing said dental floss.

* * * * *